(12) United States Patent
Lee et al.

(10) Patent No.: US 8,647,854 B2
(45) Date of Patent: Feb. 11, 2014

(54) METAGENOME-DERIVED ALKALINE PHOSPHATASE

(75) Inventors: Seung Goo Lee, Daejeon (KR); Su Lim Choi, Daejeon (KR); Eugene Rha, Daejeon (KR); Jae Jun Song, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/519,013

(22) PCT Filed: Jun. 8, 2010

(86) PCT No.: PCT/KR2010/003675
§ 371 (c)(1),
(2), (4) Date: Oct. 4, 2012

(87) PCT Pub. No.: WO2011/078448
PCT Pub. Date: Jun. 30, 2011

(65) Prior Publication Data
US 2013/0040366 A1   Feb. 14, 2013

(30) Foreign Application Priority Data
Dec. 23, 2009   (KR) ........................ 10-2009-0130205

(51) Int. Cl.
*C12N 9/16*   (2006.01)
(52) U.S. Cl.
USPC ........................................................ 435/196
(58) Field of Classification Search
USPC ........................................................ 435/196
See application file for complete search history.

(56) References Cited

U.S. PATENT DOCUMENTS 8,101,355 B2   1/2012 Lee et al.

FOREIGN PATENT DOCUMENTS

KR   1020050116672 A   12/2005

OTHER PUBLICATIONS

Handelsman, JO, et al.; "Molecular biological access to the chemistry of unknown soil microbes: a new frontier for natural products," Chemistry & Biology, 1998, pp. R245-R249, vol. 5.
Chen, Kevin, et al.; "Bioinformatics for Whole-Genome Shotgun Sequencing of Microbial Communities," PLoS Computational Biology, 2005, pp. 0106-0112, vol. 1, e24.
Venter, J. Craig, et al.; "Environmental Genome Shotgun Sequencing of the Sargasso Sea," Science, 2004, pp. 66-74, vol. 304.
Beggah, S., et al.; "Mutatnt HbpR transcription activator isolation for 2-chlorobiphenyl via green fluorescent protein-based flow cytometry and cell sorting," Microbiology Biotechnology, 2008, pp. 68-78, vol. 1, Abstract.
Neuenschwander, Martin, et al; "A simple selection strategy for evolving highly efficient enzymes," Nature Biotechnology, 2007, pp. 1145-1147, vol. 25.
NG, Lee Ching, et al.; "Genetic Evidence for Interdomain Regulation of the Phenol-responsive o54—dependent Activator DmpR," The Journal of Biological Chemistry, 1996, pp. 17281-17286, vol. 271.
HA, Jae-Seok, et al.; "Design and Application of Highly Responsice Fluorescence Resonance Energy Transfer Biosensors for Detection of Sugar in Living Saccharomyces cerevisiae Cells," Applied and Environmental Microbiology, 2007, pp. 7408-7414, vol. 73.
Zhang, Youming, et al.; "DNA cloning by homologous recombination in Escherichia coli," Nature Biotechnology, 2000, pp. 1314-1317, vol. 18.
Zhang, Youming, et al.; "A new logic for DNA engineering using recombination in Escherichia coli," Nature Genetics, 1998, pp. 123-128, vol. 20.
Jiang, Chengjian, et al.; "Characterization of a Novel Beta-Glucosidase—Like Activity from a Soil Metagenome," The Journal of Microbiology, 2009, pp. 542-548, vol. 47.
Chen, I-Chien, et al.; "Isolation and Characterization of a Novel Lysine Racemase from a Soil Metagenomic Library," Applied and Environmental Microbiology, 2009, pp. 5161-5166, vol. 75.
Kim, Jin-Seog, et al.; "Production of porphyrin intermediates in Escherichia coli carrying soil metagenomic genes," FEMS Microbiology Letters, 2009, pp. 42-49, vol. 295.
Wei, Ping, et al.; "Characterization of two soil metagenome-derived lipases with high specificity for p-nitrophenyl palmitate," Archives of Microbiology, 2009, pp. 233-240, vol. 191.
Schipper, C., et al.; Metagenome—Derived Clones Encoding Two Novel Lactonase Family Proteins Involved in Biofilm Inhibition in Pseudomonas aeruginosa, Applied and Environmental Microbiology, 2009, pp. 224-233, vol. 75.
International Search Report, Jan. 31, 2011.

*Primary Examiner* — Suzanne M Noakes
(74) *Attorney, Agent, or Firm* — Tristan A. Fuierer; Moore & Van Allen, PLLC

(57) ABSTRACT

The present invention relates to a metagenome-derived alkaline phosphatase, and more particularly to a novel, metagenome-derived alkaline phosphatase screened using a artificial genetic circuit that detects phenolic compounds, and a preparation method thereof. A novel alkaline phosphatase according to the present invention has high activity of dephosphorylating DNA and can be inactivated rapidly by simple heat treatment. Thus, it can be used for a dephosphorylation reaction so that genetic manipulations, including genetic cloning, become efficient. In addition, it can be actively expressed in recombinant microorganisms, and thus can be used in various assays, including enzyme immunoassay.

10 Claims, 8 Drawing Sheets

(A)

(B)

(A)

(B)

(C)

(A)

(B)

METAGENOME-DERIVED ALKALINE PHOSPHATASE

CROSS-REFERENCE TO RELATED APPLICATIONS

This application is filed under the provisions of 35 U.S.C. §371 and claims the priority of International Patent Application No. PCT/KR2010/003675 filed on 8 Jun. 2010 entitled "METAGENOME-DERIVED ALKALINE PHOSPHATASE" in the name of Seung Goo LEE, et al., which claims priority to Korean Patent Application No. 10-2009-0130205 filed on 23 Dec. 2009, both of which are hereby incorporated by reference herein in their entirety.

TECHNICAL FIELD

The present invention relates to a metagenome-derived alkaline phosphatase, and more particularly to a novel, metagenome-derived alkaline phosphatase screened using a artificial genetic circuit that detects phenolic compounds, and a preparation method thereof.

BACKGROUND ART

Alkaline phosphatases (EC 3.1.3.1) are enzymes that are widely distributed from microorganisms to humans and hydrolyze phosphoric monoesters to produce inorganic phosphoric acids. Alkaline phosphatases are generally known to be metal-dependent enzymes that have low substrate specificity and require metal ions such as magnesium ions ($Mg^{2+}$) or zinc ions ($Zn^{2+}$) for enzymatic reactions. Typical alkaline phosphatases include bacterial alkaline phosphatase (BAP), calf intestinal alkaline phosphatase (CIAP), shrimp alkaline phosphatase (SAP) and the like. Particularly, alkaline phosphatases are industrial enzymes which are widely used in the industrial fields, including the molecular biology field. Alkaline phosphatases are used in genetic manipulations such as cloning. Specifically, alkaline phosphatase is used to remove a phosphoric acid molecule from the ends of a vector in order to prevent self-ligation of the vector after the vector is digested with restriction enzymes for an insertion of a target gene. In addition, alkaline phosphatase is used as a typical reporter protein together with peroxidase in antibody-based immunoassays such as enzyme-linked immunosorbent assay or Western blotting, and otherwise it is also used to measure the effect of milk pasteurization. Enzymes having activities similar to alkaline phosphatase include phytase and pyrophosphatase. Phytase is an industrially highly valuable enzyme which is used for feed and environmental treatment, and pyrophosphatase is used to increase the efficiency of polymerase chain reaction (PCR).

Meanwhile, Handelsman et al. define a metagenome as collective genomes of all microorganisms in a given habit (Handelsman et al., (1998) *Chem. Biol.* 5: R245-R249). However, in recent years, the term "metagenome" refers to a collection of clones, including genomes or genes extracted from environmental samples, and a series of studies related to the metagenome are also defined as metagenomics (Chen et al., (2005) *PLoS Comput. Biol.* 1(2): 24). In studies related to the metagenome, Venter et al. (Venter et al., (2004) *Science* 304: 66-74) conducted a new conceptual study (entitled "Ecosystem sequencing") under the support of the US Department of Energy (DOE) and determined about 1 billion nucleotide sequences by whole-genome shotgun sequencing of a metagenomic library constructed from seawater samples collected from the Bermuda Triangle. The results of the shotgun sequencing indicated that the collected seawater samples contained at least 1800 microbial genomic species, including 140 unknown phylotype bacteria, and 12 millions or more new genes were found. Metagenomic studies are well suited for the purpose of using microorganisms which are difficult to culture or impossible to culture, and such metagenomic studies are molecular biology approaches which comprise extracting all DNAs in a specific environment if the microorganisms of interest are impossible to isolate by culture.

In recent years, studies on the use of directed molecular evolution technology to ensure new genetic sources from microbial genomes or metagenomes or improve the activities of existing genes to develop highly useful biocatalysts have received attention as an important strategy of biotechnology. Thus, there have been attempts to screen various enzymes using new high-sensitivity screening technologies of rapidly sensing the activities of very small amounts of enzymes.

Methods of selecting new enzymatic genes from massive gene libraries such as microbial genomes or metagenomes include a sequence-based screening method comprising performing polymerase chain reaction (PCR) based on DNA nucleotide sequences and selecting the amplified genes. This method has advantages in that the utility thereof increases day by day as genomic information increases rapidly and in that only desired genes can be specifically screened. However, this method has a disadvantage in that subjects to which the method can be applied are limited to some genetic sources, because the method can be used only in the case in which accurate information on the nucleotide sequence of a target gene is known.

In addition to this method, a function-based screening method of screening genes based on the genetic functions (i.e., enzymatic activities) is also widely used. This method has an advantage in that it can screen new unknown genes based on the enzymatic activities. However, this method has a limitation in that a screened strain should have a cluster of all activity-related genes in order to have activity and should be able to be expressed in a library host strain (e.g., *E. coli*).

In this context, studies on genetic circuitries which sense the activity of enzymes such as intracellular protease using genetic engineering technology based on the principle of transcriptional activity of yeast 3-hybride have received attention. Furthermore, there have been active studies on the technology of detecting enzymatic activity using microbial metabolic pathways designed such that metabolic products of foreign enzymes provide nutrient sources to cells. Also, technology of introducing a transcription regulatory protein, derived from microorganisms, into recombinant *E. coli* and sensing the enzymatic activity of the foreign gene in the recombinant *E. coli* has been actively studied. In addition, an effort has been actively made to develop protein engineering technology for improving the substrate specificity of regulatory proteins. For example, in one study, the regulatory protein HbpR that binds to 2-hydroxybiphenyl (2-HBP) was improved such that it specifically recognizes 2-chlorobiphenyl (2-CBP) having a chloro group in place of a hydroxyl group (Beggah et al., (2008) *Microb. Biotechnol.* 1(1): 68-78). In particular, studies on screening new enzymes using genetic circuitries that sense reaction products based on regulatory proteins have received a great deal of attention as a new technology for screening enzymatic activities.

Accordingly, the present inventors have made extensive efforts to screen new active enzymes, derived from metagenomes, by detecting various enzymatic activities with high sensitivity, and as a result, have constructed an artificial genetic circuit capable of detecting various phenolic compounds, and recovered and purified a novel gene having alkaline phosphatase enzymatic activity from a metagenomic library by screening using the genetic circuit in a high-throughput manner, thereby completing the present invention.

DISCLOSURE OF INVENTION

It is a main object of the present invention to provide a novel alkaline phosphatase having the amino acid sequence represented by SEQ ID NO: 1.

Another object of the present invention is to provide a gene encoding said alkaline phosphatase and a recombinant vector containing the gene.

Still another object of the present invention is to provide a recombinant microorganism obtained by introducing said gene or recombinant vector into a host microorganism.

Yet another object of the present invention is to provide a method of producing an alkaline phosphatase by culturing said recombinant microorganism to produce an alkaline phosphatase, and then recovering the produced alkaline phosphatase.

To achieve the above objects, the present invention provides a novel alkaline phosphatase having the amino acid sequence represented by SEQ ID NO: 1.

The present invention also provides a gene encoding said alkaline phosphatase, a recombinant vector containing the gene, and a recombinant microorganism containing said gene or recombinant vector.

The present invention also provides a method of producing an alkaline phosphatase, the method comprising culturing said recombinant microorganism to produce an alkaline phosphatase, and then recovering the produced alkaline phosphatase.

Other features and embodiments of the present invention will be more apparent from the following detailed descriptions and the appended claims

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

In the present invention, a metagenomic library is constructed by collecting a microbial community in nature or a specific area (a hot spring, a farm, compost, or an oil-contaminated soil), extracting a genome from the microbial community and introducing the extracted genome into a vector.

Enzymatic reactions that involve phenolic compounds as reaction substrates or products are very various, and phenolic compounds are not easily degraded in *E. coli* cells. Thus, even very small amounts of reaction products produced by enzymatic reactions can be detected with high sensitivity. In recent years, studies on controlling the range of sensitivity and quantitative activity of promoters by controlling the intracellular stability of reporter proteins have been reported (Neuenschwander et al., (2007) *Nature Biotech*. 25(10): 1145-1147).

The present inventors paid attention to the fact that various substrates capable of releasing phenolic compound can be used in enzymatic reactions. Based on this fact, a new synthetic biological artificial genetic circuit (genetic enzyme screening system (GESS)) which senses a phenolic compound was constructed. The constructed genetic circuit was introduced into a microorganism, and then a particular phenolic compound-containing substrate was added to the microorganism, followed by measuring the quantitative activity of a reporter (such as a fluorescence reporter, an antibiotic resistance reporter and the like) which was expressed by detecting a phenolic compound produced by the reaction between the substrate and a specific enzyme present in the metagenomic library, thereby isolating and recovering an alkaline phosphatase from the metagemonic library.

Figure 1:
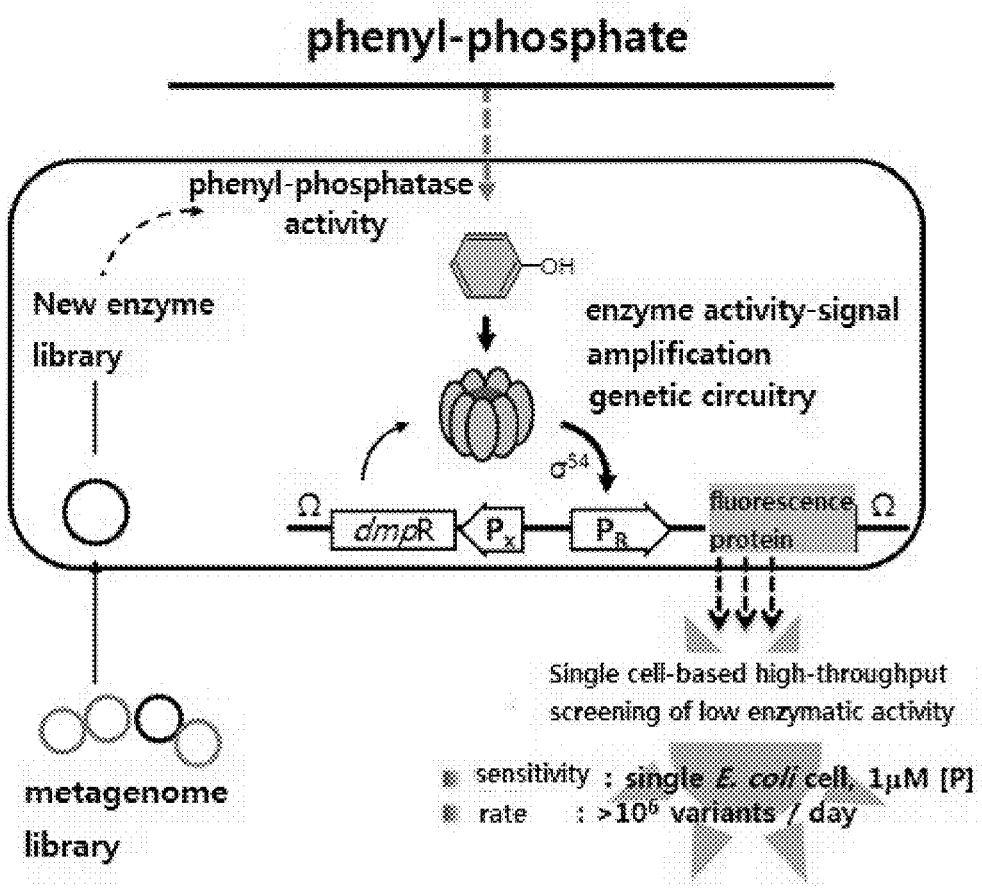
FIG. 1 is a schematic diagram showing a method capable of high-throughput screening genes having alkaline phosphatase activity from a metagenome using the genetic enzyme screening system (GESS) that can detect enzymatic activities in living cells.

FIG. 1 shows a method of screening and recovering the alkaline phosphatase of the present invention from the above metagenomic library. As shown in FIG. 1, a genetic circuit comprising a reporter which senses a phenolic compound is constructed, and an environment-derived metagenomic library is constructed. The constructed genetic circuit and the constructed metagenomic library are sequentially or simultaneously transformed into a suitable microorganism. The microorganism is treated with the substrate phenyl phosphate, followed by measuring the quantitative activity of the reporter (such as a fluorescence reporter, an antibiotic resistance reporter and the like) which is expressed by phenol which is produced by the reaction of alkaline phosphatase from the metagenomic library. And thereby it was screened and recovered a novel alkaline phosphatase from the metagenomic library.

The artificial genetic circuit (genetic enzyme screening system (GESS)) according to the present invention comprises a phenolic compound-degrading enzyme regulatory protein region (transcriptional regulation factor (TRF)), a gene expression regulatory region comprising a promoter, and at least one reporter region selected from among a fluorescence protein and an antibiotic resistance gene. TRF is a transcriptional regulation factor and is a region that encodes a regulatory protein recognizing a phenolic compound. For example, TRF may consist of dmpR. In addition, the gene expression regulatory region may be composed of the following three regions: a promoter ($P_x$) for regulating the expression of the regulatory protein (transcriptional regulation factor) recognizing the phenolic compound; an operator for reporter (OpR) to which the regulatory protein recognizing the phenolic compound binds to regulate the expression of a reporter gene located downstream thereof; and a promoter ($P_R$) for regulating the expression of the reporter. In addition, the artificial genetic circuit may comprise RBS (ribosome binding site), a forward transcriptional terminator (t▶), a reverse transcriptional terminator (◀t) and the like. The phenolic compound-degrading enzyme regulatory protein inhibits the transcription of the reporter in the absence of a phenol molecule, but binds to the OpR (Operator for Reporter) in the presence of a phenol molecule to activate the transcription of the reporter protein, and the transcription of the reporter protein is regulated in a $\sigma^{54}$-dependent manner.

The dmpR is the $\sigma^{54}$-dependent transcriptional activity regulatory factor of dmp operon containing phenolic compounds degrading genes. The *P. putida* dmp operon consists of 15 genes, and among these genes, dmpKLMNOP encodes enzymes required for phenol hydroxylation, and dmpQBC-DEFGHI encodes enzymes of the meta-degradation pathway, which degrade a catechol intermediate. It is known that the expression of the dmpKLMNOP operon is activated by the binding of the $\sigma^{54}$-dependent transcriptional regulator dmpR to the dmp operator located upstream of dmpK, and a transcriptional regulator for dmpR itself is $\sigma^{70}$-dependent (Lee et al., (1996) *J. Biol. Chem*. 271 (29): 17281-17286).

In one aspect, the present invention is directed to a novel metagenome-derived alkaline phosphatase and its encoding gene obtained by said screening method. Preferably, the alkaline phosphatase may have the amino acid sequence represented by SEQ ID NO: 1. In addition, preferably, the said enzymes-encoding gene may be represented by the nucleotide sequence of SEQ ID NO: 2.

The alkaline phosphatase according to the present invention shows the following characteristics:

(i) It has optimal activity at an alkaline pH of 8.5-9.0, preferably a pH of 9.0, and a temperature of 30-40° C., preferably 35° C.

(ii) It is inactivated by heat so that it could be controlled by heat easily. The remaining activity is below three percentage points (that are the margin of error) at 65° C.

In the present invention, the alkaline phosphatase can degrade phosphorus-ester bonds having various lengths and is a metal-dependent enzyme. Particularly, it is characterized in that the enzymatic activity of the alkaline phosphatase is increased by calcium ions.

In addition, the alkaline phosphatase according to the present invention has an activity of dephosphorylating double-strand DNA, and thus it recognizes a phosphorus molecule introduced into DNA (or double-strand DNA) to dephosphorylate the DNA. Accordingly, it can be advantageously used in the genetic manipulation-related industrial field.

The scope of the present invention includes, not only the alkaline phosphatase having the amino acid sequence of SEQ ID NO: 1, but also variants and fragments thereof, which have amino acid sequences that differ from that of the alkaline phosphatase due to the deletion, insertion or substitution of amino acid residues, or a combination thereof, within the range that does not affect the function of the alkaline phosphatase. Amino acid replacements which do not significantly change the activity of the alkaline phosphatase are known in the art.

In addition, the alkaline phosphatase may further be modified by phosphorylation, sulfation, acrylation, glycosylation, methylation, farnesylation or the like. Thus, the present invention encompasses polypeptides or their fragments, which have substantially the same amino acid sequences as that of the alkaline phosphatase. As used herein, the expression "substantially the same amino acid sequences" refers to those having a homology of at least 80%, more preferably at least 90%, and more preferably at least 95% to the amino acid sequence of SEQ ID NO: 1.

Herein, a gene that encodes the enzyme may comprise a nucleotide sequence having a sequence identity of at least 70%, preferably at least 80%, more preferably at least 90%, even more preferably at least 95% to SEQ ID NO: 2.

As used herein, the term "sequence identity" refers to the sequence similarity of residues between two polynucleotides. The above "sequence identity" can be determined by comparing the two sequences aligned in an optimal state over the sequence region to be compared. Herein, the polypeptide to be compared may have addition or deletion (for instance, gap, overhang and the like) as compared to a reference sequence (for instance, consensus sequence and the like) for an optimal alignment of the two sequences. Sequence identity between nucleic acid sequences is determined using sequencing software, for example BLASTN or FASTA.

The gene encoding the alkaline phosphatase of the present invention can be isolated or prepared using standard molecular biology techniques. For example, it can be isolated by PCR using suitable primer sequences and can also be prepared by standard synthesis techniques using an automatic DNA synthesizer.

In another aspect, the present invention is directed to a gene encoding said alkaline phosphatase, a recombinant vector containing the gene, and a recombinant microorganism containing said gene or recombinant vector.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably because most vector is a type of plasmid which is replicated independently.

In addition, the nucleotide sequence is operably linked when it is arranged in a functional relationship with another nucleic acid sequence. It may be a gene and a control sequence(s) linked to be capable of expressing the gene when a suitable molecule (e.g., transcription-activating protein) binds to a control sequence(s). Generally, the term "operably linked" means that the DNA linked sequences are contiguous, and in the case of the secretary leader sequence, are contiguous and present in a reading frame.

The transformed recombinant microorganism that is used in the present invention may be a host cells in which DNA is highly efficiently introduced and expressed. Examples thereof include all microorganisms, including eukaryotic and prokaryotic microorganisms, bacteria, yeasts, and fungi.

The transformed recombinant microorganism can be prepared according to any transformation method. As used herein, the term "transformation" means that external DNA is introduced into a host so that the DNA can be replicated with a chromosomal factor or by chromosomal integration, thereby artificially causing genetic changes. General examples of the transformation method include electroporation, calcium phosphate ($CaPO_4$) precipitation, calcium chloride ($CaCl_2$) precipitation, microinjection, a lithium acetate-DMSO method, etc.

In still another aspect, the present invention is directed to a method of producing an alkaline phosphatase, the method comprising culturing said recombinant microorganism to produce an alkaline phosphatase, and then recovering the produced alkaline phosphatase In the present invention, to culture the microorganism or to recover the alkaline phosphatase, any method may be used without particular limitation, so long as it is generally used in the art.

In the present invention, for better expression of the alkaline phosphatase, the recombinant microorganism is preferably cultured at 10-20° C. More preferably, the recombinant microorganism is cultured at 13-15° C., so that the alkaline phosphatase is obtained in a soluble form, thereby improving the solubility of the alkaline phosphatase.

In the present invention, the alkaline phosphatase produced in the recombinant microorganism can be purified by various known methods, for example, affinity chromatography, ion exchange chromatography, size exclusion chromatography and the like.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Construction of Metagenomic Library Derived from Oil-contaminated Soil

In order to construct a metagenomic library, a microbial community (accession number KCTC 11077BP) derived from oil-contaminated soil was obtained from the Korean Collection for Type Cultures, the Korea Research Institute of Bioscience and Biotechnology, and total genomic DNA was isolated therefrom and cut to suitable size using a physical method. The size of the genomic DNA fragments was measured using 0.4% agarose gel, and as a result, it was found that the genomic DNA was cut to various sizes. The cut genomic DNA was end-repaired using the end-repair enzyme mix and electrophoresed. Then, the end-repaired DNA having a size of about 30 kb was recovered from the gel and used as a DNA fragment for constructing a metagenomic library. The about 30 kb DNA fragment was ligated with a pCC1FOS vector (Epicentre, USA), and the fosmid clone was packaged using the packaging extract. The fosmid clone-packaged phage was mixed with E. coli EPI300 (Epicentre, USA) and allowed to stand at 37° C. for 45 minutes, thereby inducing infection of the phage. Then, the cells were plated on LB medium (10 g tryptone, 5 g yeast extract, 10 g NaCl, and 1.5 g agar) supplemented with 12.5 µg/ml of chloramphenicol and were sufficiently cultured at 37° C. for 30-40 hours. Then, the number of the cells was counted and the total size of the library was calculated. As a result, the diversity of the metagenomic library was about $8 \times 10^4$.

The total size of the metagenomic library constructed as described above was about 400 Mb, and because the average genomic size of microorganisms is assumed to be about 4 Mb, the genomic library was concluded to have information on about 100 or more genomes.

To analyze the metagenomic library, 5 transformants were randomly tested. The E. coli colonies that metagenomic library DNA were cultured by vigorously shaking in LB liquid medium (per liter, 10 g of tryptone, 5 g of yeast extract, and 10 g of NaCl) supplemented with 12.5 µg/ml of chloramphenicol and 1× copy-control solution (Epicentre, USA) for 5 hours, and then DNA was isolated therefrom and completely digested with BamH I and EcoR I, and the DNA fragments added to the fosmid vector were analyzed. The sizes of the DNA fragments were summed up and the size of the fosmid vector was subtracted. As a result, the size of the DNA fragments added to the fosmid vector was about 27-35 kb, and the average size thereof was about 30 kb.

Example 2

Construction of Artificial Genetic Circuit Comprising Fluorescence Protein as Reporter In order to construct an artificial genetic circuit for phenol detection comprising an EGFP (enhanced green fluorescence protein) gene as a reporter, a pMGFP plasmid (Ha et al. (2007) *Appl. Environm. Microbiol.* 73(22): 7408-7414) was digested with EcoR I and Hind III restriction enzymes to obtain a 720-bp EGFP fragment. Then, the EGFP fragment was introduced into a pUC19 vector (NEB, USA) to construct pUC-EGFP.

In the present invention, a *P. putida* colony was amplified by PCR using forward and reverse primers (SEQ ID NOS: 3 and 4), thus preparing a 2,157-bp DNA fragment (SEQ ID NO: 5) comprising: a dmpR gene (1,692 bp) comprising an EcoR I restriction enzyme linker; a dmp operator-promoter region; and a partial portion of dmpK gene (42 bp) and a restriction enzyme sequence (12 bp) inserted during the cloning process. The dmpK gene was located (1,693-2,097 bp) in upstream of 405-bp apart from dmpR, and the reporter gene was followed by 42-bp of the N-terminal region of dmpK.

```
SEQ ID NO: 3:
5'-ccggaattcgagctgatcgaaagtcgg-3'

SEQ ID NO: 4:
5'-ccggaattcctagccttcgatgccgat-3'
```

Figure 2:
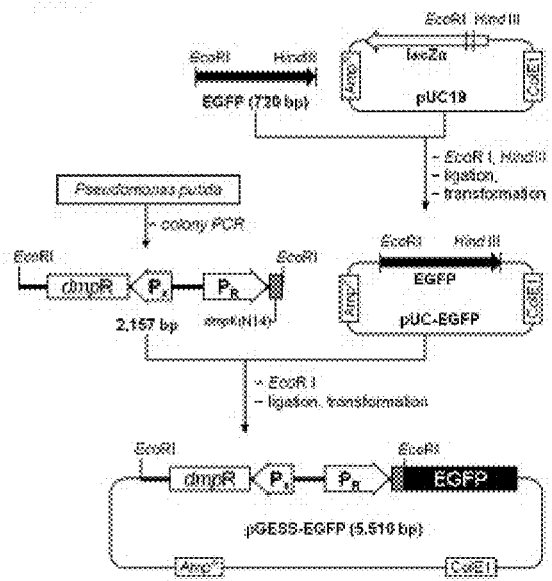
FIG. 2 is a schematic diagram showing recombinant genetic circuits constructed by genetic manipulation. (A): the genetic circuit (pGESS-EGFP) comprising EGFP as a reporter; and (B): the genetic circuit (pGESS-GFP$_{UV}$) comprising GFP$_{UV}$ as a reporter.
Figure 2:
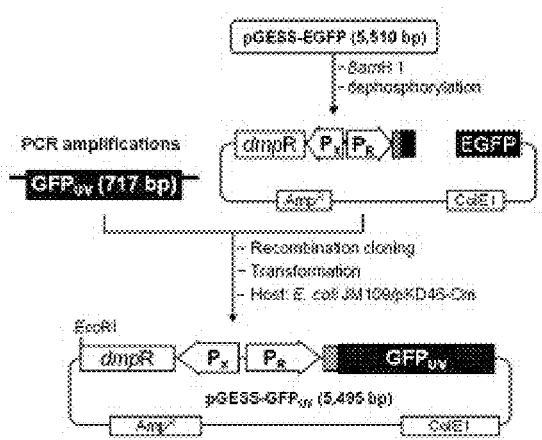

The partial N-terminal fragment of dmpK was allowed to remain in order to stably maintain the transcription enhancer function of the dmp operator-promoter region even if various fluorescence proteins or antibiotic resistance proteins were used as the reporter. The PCR product was cloned into the EcoR I site of pUC-EGFP, thereby constructing pGESS-EGFP (5,510 bp) (see FIG. 2A).

Also, in the present invention, in order to use a $GFP_{UV}$ gene advantageous for visual observation as the reporter gene in the system of the present invention, a 717-bp $GFP_{UV}$ gene derived from $pGFP_{UV}$ (Clontech, USA) was introduced in place of EGFP. For this purpose, the $GFP_{UV}$ gene was amplified by PCR using forward and reverse primers (SEQ ID NOS: 6 and 7) and introduced into a pGESS-EGFP vector by homologous recombination (see FIG. 2B). The homologous combination was performed by preparing a host cell and introducing a linearized gene in the host cell (Zhang et al., (2000) Nature Biotech. 18: 1314-1317; Zhang et al., (1998) Nature Genetics, 20: 123-128; Lee Seung-Goo et al., (2005), Korea Patent Application No. 10-2005-0116672). Single colonies of E. coli DH5α containing a pKD46 vector encoding λ-red recombinase were inoculated into 3 ml of LB liquid medium supplemented with 25 μg/ml of chloramphenicol and were shake-cultured at 30° C. for 16 hours. The culture medium was inoculated at 1% (v/v) into 100 ml of LB liquid medium supplemented with 25 μg/ml of chloramphenicol and 50 mM arabinose and was shake-cultured at 30° C. until the cell growth ($OD_{600}$/ml) reached 0.5-0.6. After completion of the culture, competent cell for electroporation was prepared (Molecular Cloning: A Laboratory Manual, Joseph Sambrook, David W. Russell), and 10 ng of pGESS-EGFP digested with BamH I and 100 ng of the PCR product of $GFP_{UV}$ were added to the competent cells, which were then electroporated (18 kV/cm, 25 μF). Then, 1 ml of SOC medium was added to the cells, after which homologous recombination between the vectors was induced at 25° C. for 20 hours. Then, the cells were plated on LB solid medium supplemented with 50 μg/ml of ampicillin and were cultured at 37° C. overnight, and a phenol sensor substituted with the $GFP_{UV}$ gene, that is, $pGESS-GFP_{UV}$, was selected. For reference, the pKD46 vector contained a temperature sensitive origin of replication, and thus was removed at 37° C., and cells introduced with only the $pGESS-GFP_{UV}$ gene were obtained.

```
SEQ ID NO: 6:
5'-acctggagatggccgtgaccaataccccacaccgactttcgatc agctcatgagtaaaggagaagaact-3'

SEQ ID NO: 7:
5'-cggataacaatttcacacaggaaacagctatgaccatgattacgc caagcttatttgtagagctcatcca-3'
```

Example 3

Figure 3:
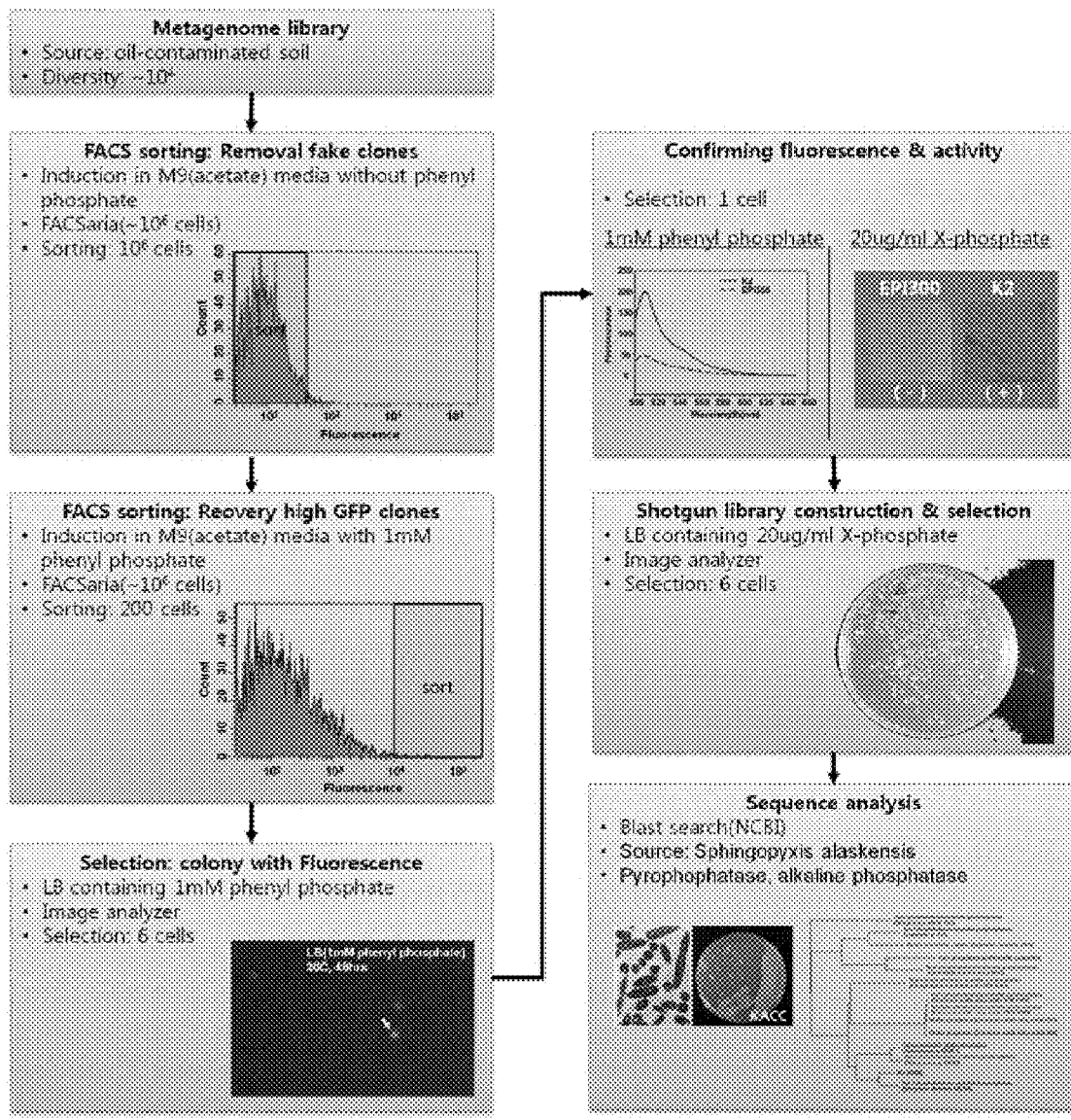
FIG. 3 shows a process of screening alkaline phosphatases from a metagenomic library using the genetic enzyme screening system (GESS).

High-throughput Screening of Alkaline Phosphatase from Environment-derived Metagenome The $pGESS-GFP_{UV}$ constructed in Example 2 was introduced by electroporation into the metagenomic library constructed in Example 1, and the high-throughput screening of phosphatases using the GESS system was attempted (see FIG. 3).

The metagenomic library introduced with $pGESS-GFP_{UV}$ was concentrated with storage buffer (per liter, 1×TY medium (8 g of tryptone, 5 g of yeast extract, 2.5 g of NaCl), 15% (v/v) glycerol, and 2% (v/v) glucose) to a concentration of about $10^{10}$ cells/ml, and 0.5 ml was dispensed into a 1.5-ml tube and stored in a deep freezer.

The $pGESS-GFP_{UV}$-containing metagenomic library stored in the deep freezer was inoculated into 10 ml of LB medium at a concentration of 1% (v/v) (about $10^8$ cells) and incubated at 37° C. for 12 hours, thus preparing a healthy library. The cell culture was inoculated into 2 ml of LB medium at a concentration of 1% (v/v) and cultured at 37° C. until the cell concentration ($OD_{600}$/ml) reached about 2.5-3 (about 5-6 hours), after which the library was recovered by concentration (4000 rpm, 10 min). The library was washed with M9 medium (per liter, 12.8 g of $Na_2HPO_4.7H_2O$, 3 g of $KH_2PO_4$, 0.5 g of NaCl, 1 g of $NH_4Cl$, 2 mM $MgSO_4$, 0.1 mM $CaCl_2$, 0.4% (w/v) glucose, 0.01% (w/v) thiamine), and it was centrifuged (4000 rpm, 10 min) and suspended. Then, in order to remove a false positives clone that emits fluorescence even in the absence of the substrate, the cells were suspended in M9 medium containing no phenyl phosphate and shake-cultured at 30° C. for 16 hours. 1× Copy-control solution and 50 μg/ml of ampicillin and 12.5 μg/ml of chloramphenicol as selective markers were added to the medium. After the culture, $10^6$ cells which did not emit fluorescence were recovered using a fluorescent flow cytometer (FACSaria, BD, USA, 407 nm violet laser, BP Filter 530/30) while avoiding the false positive clone (fluorescent clone). The recovered cells were inoculated into LB medium and cultured at 37° C. for 12 hours or more.

Then, a test for screening a candidate group showing fluorescence was carried out using the substrate phenyl phosphate. Specifically, the recovered cell culture was inoculated into 2 ml of LB medium at 1% (v/v) and cultured at 37° C. until the cell concentration ($OD_{600}$/ml) reached about 2.5-3 (about 5-6 hours). Then, the library was recovered by centrifugation (4000 rpm, 10 min). The recovered library was washed with M9 medium, centrifuged (4000 rpm, 10 min) and suspended.

Then, the cells were suspended in M9 medium containing 1 mM phenyl phosphate and were shake-cultured at 30° C. for 16 hours, thereby performing an enzymatic reaction in the cells. 1× Copy-control solution and 50 μg/ml of ampicillin and 12.5 μg/ml of chlorampenicol as selective markers were added to the medium. After the enzymatic reaction, the fluorescent pattern of the fluorescent library was analyzed by a fluorescent flow cytometer, and about 200 cells emitting strong fluorescence were recovered.

Then, the recovered cells were plated on substrate-containing solid media, colonies emitting strong fluorescence were selected. Specifically, the cells recovered using the fluorescent flow cytometer were plated on 1 mM phenyl phosphate-containing LB solid medium and cultured at 30° C. for 48 hours, thus inducing the sufficient emission of fluorescence. To increase the expression level of the metagenomic library introduced into the fosmid vector, 1× Copy-control solution and 50 μg/ml of ampicillin and 12.5 μg/ml of chlorampenicol as selective markers were added to the medium. The fluorescent colonies were observed by an image analyzer (Gel Doc 2000 gel documentation system, Bio Rad, USA), and the analysis of the images was performed using image analysis program (Quantity One, Bio Rad, USA). As a result, 47 colonies were produced, and among them, 6 colonies presumed to emit fluorescence were selected.

To verify the enzymatic activity of the isolated clones, 5-bromo-4-chloro-3-indolyl phosphate (BCIP) was used as a color development substrate. This substrate has the same development factor as X-gal which is frequently used in molecular biology studies, and it allows the activity of phosphatase to be recognized by color development. The selected strains were streaked on LB solid media containing 20 μg/ml of BCIP and were cultured at 30° C. during a day. Whether the strains emitted color was examined, and as a result, one clone was selected.

The selected clone was cultured again on LB medium, and the same enzymatic reaction as described above was performed while the fluorescent spectrum was examined. For analysis of fluorescence, the cells subjected to the enzymatic reaction were recovered by centrifugation (4000 rpm, 10 min) and washed once with PBS buffer, and CelLytic B (Sigma, USA), 20 µg/ml lysozyme (Sigma, USA) and DNAase I (Roche, Swiss) were added thereto to lyse the cell wall. Then, the cells were centrifuged (15000 rpm, 15 min) to precipitate the cell debris, and the supernatant was extracted and the fluorescent spectrum (excitation 385 nm) was analyzed by a fluorescence spectrometer (Fluorometer, varian, Australia). As a result, it was found that fluorescence was emitted at 510 nm and was strongly emitted compared to the control group comprising the genetic circuit alone.

Example 4

Recovery and Isolation of Gene Having Alkaline Phosphatase Activity

From the fosmid clone comprising the alkaline phosphatase gene screened in Example 3, DNA was extracted, digested with Not I restriction enzyme, and then analyzed by pulse-field gel electrophoresis (PFGE). As a result, it was seen that the fosmid vector contained a gene of about 37-40 kb.

The absence of pGESS (pGESS-GFP$_{UV}$) in the clone was confirmed through inoculation into LB medium containing 50 µg/ml of ampicillin. Then, the re-screened E. coli EPI300 containing the alkaline phosphatase gene was inoculated into 100 ml of LB liquid medium containing 1× Copy-control solution and was cultured at 37° C. for 5 hours and recovered. DNA was isolated from the recovered cells using a Mini-Prep kit (midi-prep kit, Qiagen, USA). The isolated DNA was digested with Not I restriction enzyme and subjected to PFGE, and then the 37-40 kb internal gene excluding the fosmid vector was isolated and purified. Then, the gene was cut using a DNA cutter (Hydroshear, Gene Machines, USA), and a fragment having a size of about 3-7 kb was recovered and phosphorylated. As the vector, a pSTV28 (Takara, Japan) plasmid was used. The vector digested with BamH I was ligated with the phosphorylated internal gene and inserted into E. coli DH10B (Takara, Japan) by electroporation, thus constructing a shotgun library. The diversity of the library was about $4\times10^4$, and because the size of the internal size of the internal gene introduced into the fosmid vector was about 40 kb, the library included the whole of the internal gene of the selected fosmid clone. This shotgun library was introduced into E. coli DH5α containing pGESS (pGESS-GFP$_{UV}$), and 6 clones having alkaline phosphatase activity were finally selected by the screening method using the artificial genetic circuit (pGESS-GFP$_{UV}$) described in Example 2, together with and the color development substrate (BLIP).

Example 5

Comparison of Nucleotide Sequence and Homology Between Alkaline Phosphatases

Figure 4:
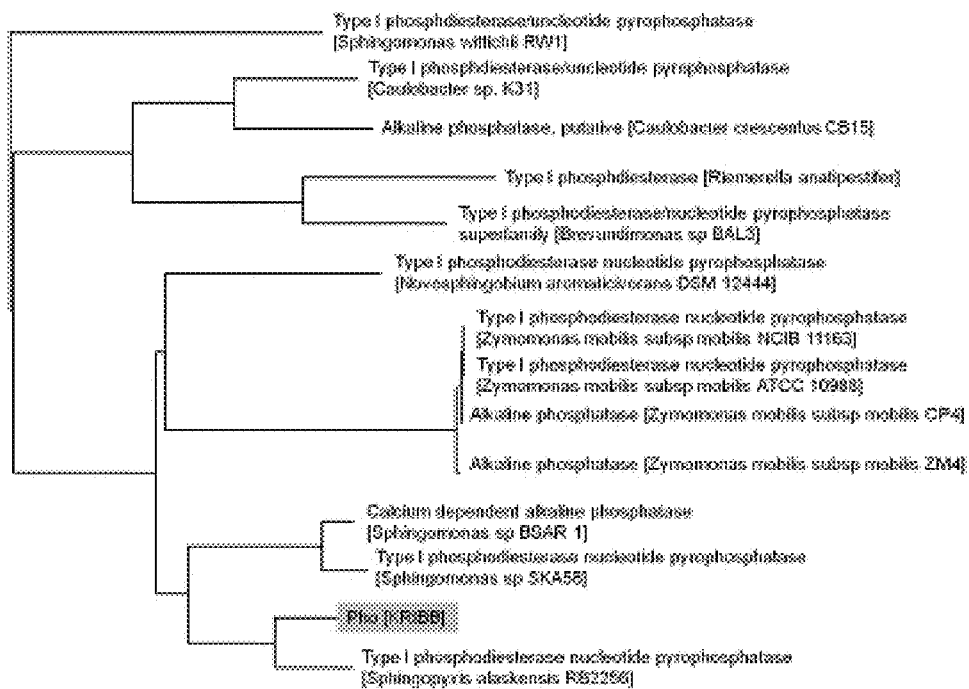
FIG. 4 shows the results obtained by performing a BLAST search based on the amino acid sequence of a novel alkaline phosphatase and then displaying sequences having high homology by the distance tree.

The 6 clones showing phenyl phosphatase activity were sequenced. As a result, the size of the internal gene of each clone was about 2.2-5.4 kb, and 2 of the 6 clones had the same, and the clones of about 3 kb were all included in the clone having the largest insert gene of 5,428 bp. The largest clone was sequenced (http://blast.ncbi.nlm.nih.gov), and as a result, it showed high homology to about 5-kb sequences including nucleotide pyrophosphatase in the genome of Sphingopyxis alaskensis RB2256, and it showed a homology of about 79% to nucleotide pyrophosphatase. Based on these result, it could be seen that the phosphatase had a size of 1,824 bp (SEQ ID NO: 2) and consisted of 607 amino acids (SEQ IID NO: 1). In the present invention, the above protein was named "alkaline phosphatase Pho". In addition, a BLAST search was performed on the amino acid sequence, and then the homology was analyzed by the distance tree. As a result, the above protein showed high homology to phosphodiesterase and alkaline phosphatase (see FIG. 4).

For reference, it is known that Sphingopyxis alaskensis RB2256 is a psychrophilic microorganism (4-10° C.) which is distributed in Alaska deep sea and present largely in the North Sea and the North Pacific Ocean and also found on land. In order for this microorganism to grow in deep sea in a state deficient in nutrients, it must be able to efficiently absorb very low concentrations of nutrients. Thus, Sphingopyxis alaskensis has a large surface area per volume, a fine size (less than 0.1 µm$^3$) and high affinity for microelements and can use various nutrients. Thus, this strain is receiving attention in the cell biology field.

Example 6

Construction of Transformant for Expression of Alkaline Phosphatase

For overexpression of the alkaline phosphatase, the alkaline phosphatase Pho described in Example 5 was cloned into a pET21a vector (Novagen, USA) which was then transformed into BL21(DE3)(RBC, Taiwan). PCR was performed using the gene (SEQ ID NO: 2) selected in Example 5 as a template and synthesized forward and reverse primers (SEQ ID NOs: 8 and 9).

SEQ ID NO: 8:
5'-gggaattccatatgtcacaatcctatgcctgtgc-3'

SEQ ID NO: 9:
5'-ccgctcgagtgaaatccttccctcgatgcggcaactgctctcgg-3'

Figure 5:
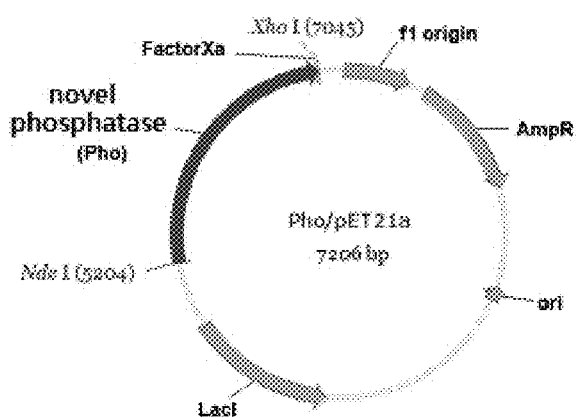
FIG. 5 shows a drawing cloned novel alkaline phosphatase into a pET21a vector to overexpress the alkaline phosphatase, in which a Nde I recognition site is located at the N-terminal end of the alkaline phosphatase, and Xho I and Factor Xa recognition sites are located at the C-terminal end.

The forward primer included a Ned I restriction site, and the reverse primer included Xho I and Factor Xa sites. The PCR was performed for 30 cycles of 30 sec at 95° C., 30 sec at 55° C. and 2 min and 30 sec at 72° C. The amplified DNA fragment was completely digested with the restriction enzymes Nde I and Xho I, and then ligated with the overexpression vector pET-21a, which has been digested with the same restriction enzymes and treated with SAP (Roche, Swiss), thereby preparing a recombinant plasmid (Pho/pET21a) for overexpression of the novel alkaline phosphatase (see FIG. 5).

The recombinant plasmid Pho/pET21a was introduced into E. coli BL21(DE3) by electroporation, thereby preparing a transformed strain (Pho/pET21a/BL21(DE3)).

Example 7

Examination of Expression Level of Alkaline Phosphatase in Transformant as a Function of Temperature To overexpress the metagenome-derived alkaline phosphatase, the expression level thereof as a function of temperature was examined. Specifically, single colonies of the transformant (Pho/pET21a/BL21(DE3)) prepared in Example 6 were inoculated into LB medium and shake-cultured at 37° C. overnight. Next day, the cell culture was inoculated into 50 ml of LB medium at 1% (v/v) and cultured at 37° C. until the cells concentration ($OD_{600}$/ml) reached 0.4-0.5. 50 µg/ml of ampicillin as a selective marker was added to the medium. 0.5 mM of IPTG (isopropyl-beta-D-thiogalactopyranoside) was added to the culture medium, and for a test at each temperature, 10 ml of the culture medium was dispensed into each baffle flask. The dispensed culture medium was incubated at 15° C., 20° C., 30° C. or 37° C. for 20 hours (at 15° C. and 20° C.) or 8 hours (at 30° C. and 37° C.). The cells were recovered by centrifugation (45000 rpm, 10 min) and washed once with 50 mM Tris-HCl buffer (pH 7.5). Then, the cells were suspended in 500 µl of the same buffer, and 200 µl of CelLytic B (Sigma, USA) was added thereto. The suspended cells were completely lysed using a sonicator (method: 3 sec lysis, 3 sec stop, for 3 min, 20% intensity, Vibra cell, Sonics, USA).

Figure 6:
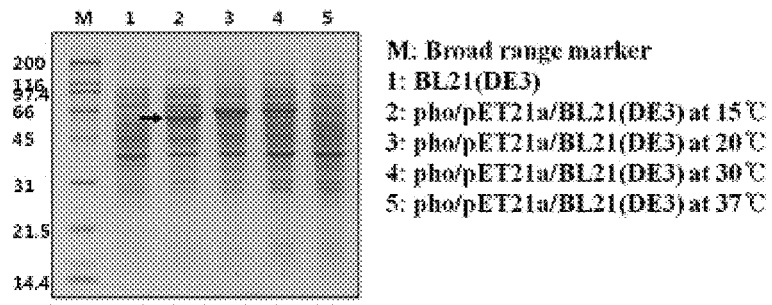
FIG. 6 is a SDS-PAGE photograph showing the results of examining the expression level of a novel alkaline phosphatase in different temperatures.

Then, the cells were subjected to SDS-PAGE (Sodium dodecyl sulfate-polyacrylamide gel electrophoresis) and stained with Coomassie brilliant blue, and the expression pattern of the protein at each temperature was analyzed. As a result, it was seen that the expression level of the megagenome-derived alkaline phosphatase was the highest at 15° C. (see FIG. 6).

Example 8

Purification of Novel Alkaline Phosphatase

In order to analyze the enzymatic characteristics of the isolated novel alkaline phosphatase, the purification of the protein was tried. Specifically, a single colony of the transformant (Pho/pET21a/BL21(DE3)) prepared in Example 6 was inoculated into LB medium and shake-cultured at 37° C. overnight. Next day, the culture medium was inoculated into 300 ml of LB media (300 ml×4 flasks) at 0.3% and cultured at 37° C. until the cell concentration ($OD_{600}$/ml) reached 0.4-0.5. 50 µg/ml of ampicillin as a selective marker was added to the medium. 0.5 mM IPTG was added to the culture medium, and the cells were shake-cultured at 15° C. for 20 hours. The cells were recovered by centrifugation (5000 rpm, 10 min), suspended in 10 ml of buffer (25 mM Tris-HCl (pH 7.6), 1 mM PMSF, 25 mM NaCl, 5 mM imidazol, 1 mM $CaCl_2$), and then lysed by sonication (method: 3 sec lysis, 3 sec stop, for 3 min, 20% intensity, Vibra cell, Sonics, USA). The cell lysate was centrifuged (4° C., 15000 rpm, 15 min) to remove the cell debris, and the supernatant was collected. The supernatant was filtered through a 0.2-µm syringe filter, thus preparing the liquid to be purified.

Purification was performed using a high-speed protein liquid separation system (AKTA FPLC UPC-900, Pharmacia, USA) and a fraction collector (Frac-900, Pharmacia, USA). In a first step, affinity chromatography was performed using His tag. Herein, a Histrap HP (GE healthcare, USA) column was used and adsorption buffer (25 mM Tris-HCl (pH 7.6), 1 mM PMSF, 25 mM NaCl, 5 mM imidazol, 1 mM $CaCl_2$) and elution buffer (25 mM Tris-HCl (pH 7.6), 25 mM NaCl, 500 mM imidazol, 1 mM $CaCl_2$) were used. In a second step, ion exchange chromatography was performed. Herein, a Hitrap Q HP (GE healthcare, USA) column, adsorption buffer (25 mM Tris-HCl (pH 7.6), 1 mM $CaCl_2$) and elution buffer (25 mM Tris-HCl (pH 7.6), 500 mM NaCl, 1 mM $CaCl_2$) were used. In a third step, size exclusion chromatography was performed. Herein, a Superose 6 HR (GE healthcare, USA) column and an elution buffer (25 mM Tris-HCl (pH 7.6), 150 mM NaCl, 1 mM $CaCl_2$) were used. In order to confirm the results of the three-step purification, SDS-PAGE was performed (see FIG. 6), and the comparison of activity between the purification steps was performed (Table 1).

TABLE 1

Change in activity according to purification step

| Purification step | Specific activity (U/mg) | Purification (fold) |
| --- | --- | --- |
| Cell extract | 123 | 1 |
| Histrap | 1528 | 12.4 |
| Hitrap Q | 1642 | 13.4 |
| Superose 6 | 1821 | 14.8 |

Figure 7:
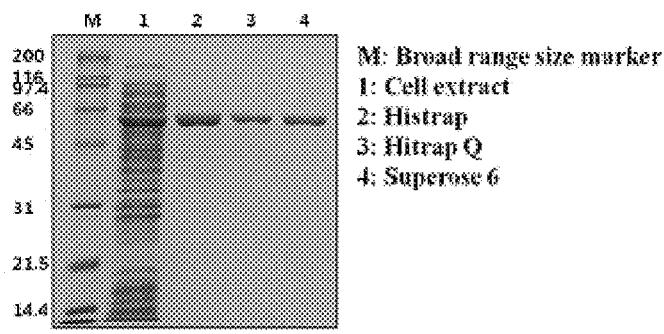
FIG. 7 is a SDS-PAGE photograph showing the results of examining the activity of a novel alkaline phosphatase as each purification step after overexpression.

From the results in Table 1 above, it was seen that the alkaline phosphatase according to the present invention was sufficiently recovered from the recombinant microorganisms even by affinity chromatography only (see FIG. 7).

Figure 8:
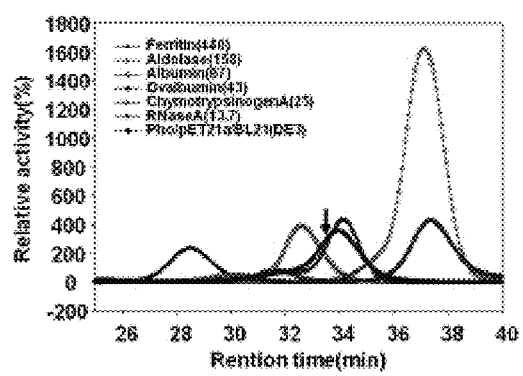
FIG. 8 shows the results of analyzing the protein binding structure of a novel alkaline phosphatase by size exclusion chromatography.

In addition, the molecular weight and oligomeric state of the purified alkaline phosphatase was analyzed by size exclusion chromatography, and as a result, it was seen that the protein was a monomer having a molecular weight between 67 kDa and 43 kDa (see FIG. 8).

Example 9

Analysis of Enzymatic Properties of Novel Alkaline Phosphatase

The alkaline phosphatase purified in Example 8 was examined for optimal pH and temperature, thermal stability, substrate specificity, and the effect of metal ions on enzymatic activity. An enzymatic reaction was carried out in the following manner. The enzymatic reaction solution used was a mixture of 50 mM diethanolamine, DEA (pH 9.0) buffer, 0.5 mM para-nitrophenylphosphate (pNPP) and the enzyme liquid purified in the purification process of Example 8, and the enzymatic reaction was carried out at 37° C. for 5 minutes. The enzymatic reaction was stopped by addition of the same amount of 1M NaOH, and the amount of nitrophenol produced by the enzymatic reaction was measured. In the measurement, a multilabel microplate reader (Victor5, Perkin-Elmer, USA) was used in order to confirm an increase in the absorbance at 405 nm. 1 unit was defined as the amount of the enzyme that can produce 1 µmol of para-nitrophenol per minute at 37° C.

(1) Examination of Characteristics in Different pH and Temperatures

Figure 9:
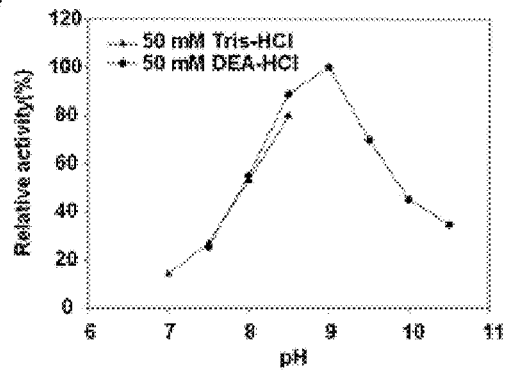
FIG. 9 shows the results of analyzing the properties of a novel alkaline phosphatase in different pH and temperatures. (A): the results of analysis carried out to determine an optimal pH showing highest activity; (B): the results of analysis carried out to determine an optimal temperature showing highest activity; and (C): the results of examining the degree of thermal inactivation of enzymes.
Figure 9:
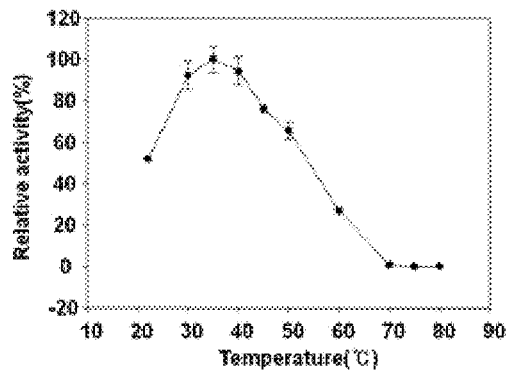
Figure 9:
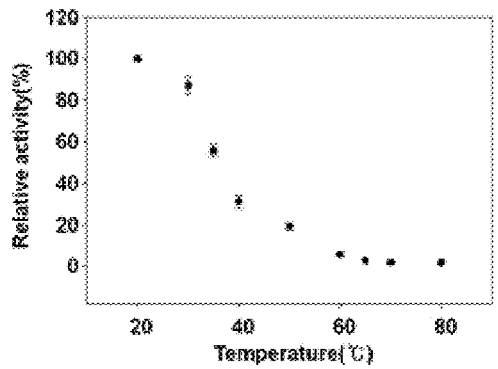

In order to examine the optimal pH of the novel alkaline phosphatase, the activity thereof was compared between a pH of 7.0 and a pH of 10.5. At a pH of 7.0-8.5, 50 mM Tris-HCl buffer was used, and at a pH of 7.5-10.5, 50 mM DEA buffer was used. The test results indicated that the novel alkaline phosphatase had the highest activity at a pH of 9.0 (see FIG. 9A).

And, the activity of the enzyme was examined in different temperatures. As a result, the activity of the enzyme was optimal at 35° C. (see FIG. 9B). In order to the thermal stability of the enzyme, the enzyme was allowed to stand at each temperature for 15 minutes, and then the activity of the enzyme was measured. As a result, it was seen that the activity of the enzyme decreased rapidly as the temperature increased, and at 65° C., only about 3% or less of the activity remained.

(2) Examination of Substrate Specificity

In order to measure the activities of novel alkaline phosphatase for various substrates, a color development reaction was carried out using a malachite green kit (BioAssay Systems, USA) according to the manufacturer's manual. The enzymatic reaction was carried out at a pH of 9.0 and at 37° C., and other reaction reactions were the same as described above.

Figure 10:
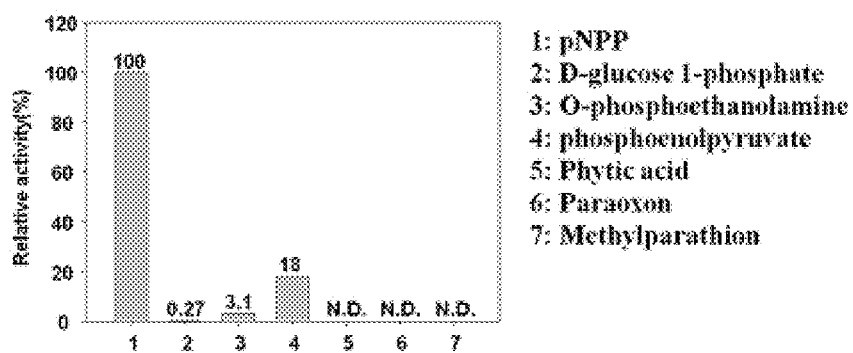
FIG. 10 shows the results of examining the substrate specificity of a novel alkaline phosphatase in various type of substrate. (A): the results of examining activity to various types of substrates; and (B): the results of examining the change in activity in different lengths of a phosphorus-ester bond.
Figure 10:
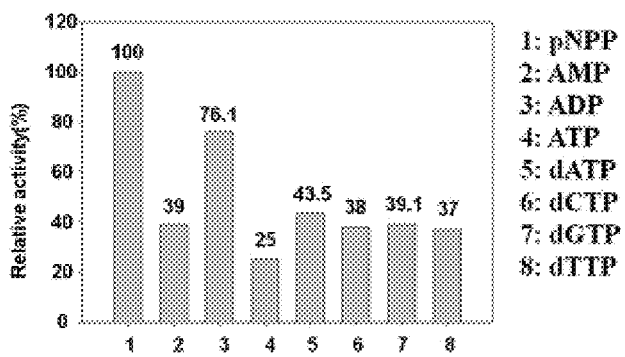

First, whether the metagenome-derived phosphatase of the present invention has industrially useful substrate-degrading activities in addition to alkaline phosphatase activity was examined. As the substrates, para-nitrophosphate (pNPP), D-glucose 1-phosphate, O-phosphoethanolamine, phosphoenolpyruvate, phytic acid, paraoxon and methylparathion were used, and the test was carried out a pH of 9.0. The test results indicated that the enzyme showed high activity for para-nitrophosphate (see FIG. 10 A).

Second, whether the enzyme of the present invention can degrade phosphorus-ester bonds having various lengths was examined. As the substrates, para-nitrophosphate (pNPP), adenosine monophosphate (AMP), adenosine diphosphate (ADP), adenosine triphosphate (ATP), deoxyadenosine triphosphate (dATP), deoxycytidine triphosphate (dCTP), deoxyguanosine triphosphate (dGTP), and deoxythymidine triphosphate (dTTP) were used. The test results indicated that the enzyme degraded phosphorus-ester bonds having various lengths (see FIG. 10B).

(3) Examination of the Effects of Metal Ions on Enzymatic Activity

The effects of various bivalent metals on the activity of the enzyme were examined. Specifically, after the enzyme liquid of the present invention has been treated with 5 mM ethylenediaminetetraacetic acid (EDTA), the EDTA was removed, and then 1 mM of each of metal ions, including nickel chloride ($NiCl_2.6H_2O$), cobalt chloride ($CoCl_2.6H_2O$), calcium chloride ($CaCl_2$), cadmium chloride ($CdCl_2$), copper chloride ($CuSO_4.5H_2O$), magnesium chloride ($MgCl_2$) and zinc sulfate ($ZnSO_4.5H_2O$), was added to the enzyme liquid which was then allowed to stand on ice for about 15 minutes. Then, the activity of the enzyme for each metal ions was measured.

Figure 11:
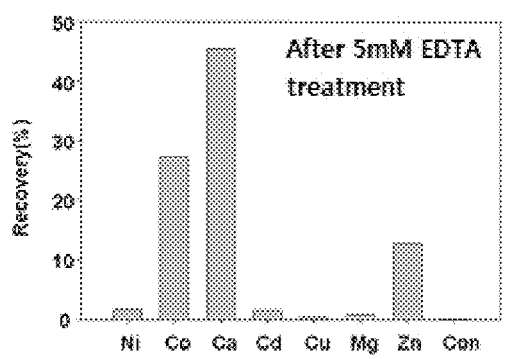
FIG. 11 shows the results of examining the effects of divalent metal ions on a novel alkaline phosphatase after treatment with EDTA.

The alkaline phosphatase according to the present invention was completely inactivated by ethylenediaminetetraacetic acid (EDTA), suggesting that it is a metal-dependent enzyme that necessarily requires metal ions. In addition, it was seen that the activity of the enzyme was most significantly increased by calcium ions (see FIG. 11).

Example 10

Effect of Novel Alkaline Phosphatase on Dephosphorylation of DNA

In order to confirm the effect of the novel alkaline phosphatase of the present invention on the dephosphorylation of double-strand DNA, the enzyme was cloned into a vector, and the dephosphorylation of the vector was examined. Also, the effect of the enzyme of the present invention was compared with that of a commercial alkaline phosphatase.

Specifically, as the substrate DNA, pUC19 DNA (NEB, USA) which is frequently used as a cloning vector was used. The DNA was linearized by digestion with restriction enzymes in order to protrude a phosphate group from the 5'-terminal end of DNA. The restriction enzymes used were Hind III, Pst I and Sma I, which create a 5'-overhang, a 3'-overhang and a blunt end, respectively (Table 2). Generally, the dephosphotylation ability of alkaline phosphatase varies depending on the terminal end shapes of linearized DNA.

TABLE 2

Restriction enzyme recognition sites and the terminal end shapes of linearized DNA after digestion

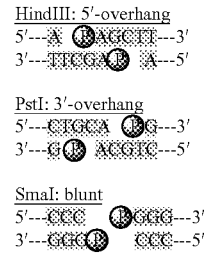

After digestion with the restriction enzymes, the pUC19 DNA was electrophoresed on agarose gel, and the 2,686-bp pUC19 band was cut out. Then, the DNA was purified by a DNA purification column (Qiagen, Germany). To 100 ng of the purified DNA, 1U of each of commercial antarctic phosphatase (NEB, USA), shrimp alkaline phosphatase (Promega, USA), calf-intestinal alkaline phosphatase (Roche, Swiss), APex™ heat-labile alkaline phosphatase (Epicentre, USA) or Pho (KRIBB; of this invention) was added, followed by a dephosphorylation reaction. The reaction was carried out according to the method recommended by each manufacturer. After the dephosphorylation reaction, each DNA was purified by a DNA purification column and self-ligated using 1U ligase (Takara, Japan) at 10° C. for 10 hours. After the ligation, 10 ng of each of the DNAs was transformed into *E. coli* competent DH5α cells (RBC, Taiwan) by heat-shock method, and the cells were plated on LB plate medium containing ampicillin (50 µg/ml) and cultured at 37° C. overnight. Then, the number of the produced transformants was compared between the phosphatase enzymes. As a control, a pUC19 DNA not treated with restriction enzymes was used. The efficiency of dephosphorylation was determined based on the decrease in number of colonies compared to the control, after transformation following the self-ligation of the DNA. This was expressed as recircularization inhibition rate (%). Re-circularization inhibition rate (%)={1−(number of colonies of sample/number of colonies of control)}×100.

The inventive novel alkaline phosphatase Pho screened from the metagenomic library showed the activity of dephosphorylating the double DNA. Specifically, the novel alkaline phosphatase showed dephosphorylation rates of 100% and 99.6% for the 5'-overhang and blunt DNAs and 91.1% for the 3'-overhang DNA. In addition, it showed high dephosphorylation effects compared to the commercial alkaline phosphatases (Table 3).

TABLE 3

Comparison of dephosphorylation activity between novel and commercial alkaline phosphatases

| Commercial AP | Restriction enzyme | Dephospholyation (%) |
|---|---|---|
| Antarctic Phosphatase (NEB) | Hind III | 99.8 |
|  | Pst I | 87.4 |
|  | Sma I | 99.4 |
| Shrimp Alkaline | Hind III | 99.5 |

TABLE 3-continued

Comparison of dephosphorylation activity between novel and commercial alkaline phosphatases

| Commercial AP | Restriction enzyme | Dephospholyation (%) |
| --- | --- | --- |
| Phosphatase (Promega) | Pst I | 98.0 |
| | Sma I | 98.9 |
| | Hind III | 99.9 |
| Calf-intestinal alkaline phosphatase (Roche) | Pst I | 98.2 |
| | Sma I | 100.0 |
| Apex ™Heat-Labile Alkaline Phosphatase (Epicentre) | Hind III | 99.8 |
| | Pst I | 95.2 |
| | Sma I | 99.7 |
| Pho (KRIBB) | Hind III | 100.0 |
| | Pst I | 91.1 |
| | Sma I | 99.6 |

INDUSTRIAL APPLICABILITY

As described above, a novel alkaline phosphatase acquired by screening from metagenome library using the genetic enzyme screening system (GESS) according to the present invention has high activity of dephosphorylating DNA and can be inactivated rapidly by simple heat treatment. Thus, it can be used for a dephosphorylation reaction so that genetic manipulations, including genetic cloning, become efficient. In addition, it can be actively expressed in recombinant microorganisms, and thus can be used in various assays, including enzyme immunoassay.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

---

What is claimed is:

1. An isolated alkaline phosphatase having the amino acid sequence represented by SEQ ID NO: 1.

2. The alkaline phosphatase of claim 1, wherein an optimal temperature of the alkaline phosphatase is 30-40° C., and an optimal pH of the alkaline phosphatase is 8.5-9.0.

3. The alkaline phosphatase of claim 1, wherein the enzymatic activity of the alkaline phosphatase is increased by calcium ions.

4. A recombinant vector comprising a gene encoding the alkaline phosphatase of claim 1.

5. An isolated recombinant microorganism comprising a gene encoding the alkaline phosphatase of claim 1.

6. A method of producing an alkaline phosphatase, the method comprising culturing the recombinant microorganism of claim 5 to produce an alkaline phosphatase, and then recovering the produced alkaline phosphatase.

7. The method of claim 6, wherein the alkaline phosphatase is produced by culturing the recombinant microorganism at 10-20° C.

8. A recombinant microorganism obtained by introducing the recombinant vector of claim 4 into a host microorganism.

9. A method of producing an alkaline phosphatase, the method comprising culturing the recombinant microorganism of claim 8 to produce an alkaline phosphatase, and then recovering the produced alkaline phosphatase.

10. The method of claim 8, wherein the alkaline phosphatase is produced by culturing the recombinant microorganism at 10-20° C.

\* \* \* \* \*

SEQUENCE LISTING

<160> NUMBER OF SEQ ID NOS: 9

<210> SEQ ID NO 1
<211> LENGTH: 607
<212> TYPE: PRT
<213> ORGANISM: Artificial Sequence
<220> FEATURE:
<223> OTHER INFORMATION: Synthetic Construct

<400> SEQUENCE: 1

```
Met Ser Gln Ser Tyr Ala Cys Ala Asn Pro Leu Ser Ala Arg Arg Arg
1               5                   10                  15

Ser Ser Arg Gln Gly Leu Pro Tyr Arg Arg Leu Ser Pro Arg Gly Gln
            20                  25                  30

Pro Ala Pro Thr Pro Leu Ala Arg Arg Ser Cys Pro Val Thr Phe Lys
        35                  40                  45

Tyr Leu Ala Thr Ala Leu Ala Ala Thr Leu Ser Ile Ala Ala Thr Gly
    50                  55                  60

Ala Val Val Ala Gln Asp Arg Ala Pro Ala Pro Val Ala Pro Ala
65                  70                  75                  80

Ala Lys Val Thr Ala Ala Thr Pro Ala Pro Lys Leu Val Ile Ala Ile
                85                  90                  95

Ser Val Asp Gln Phe Ser Ala Asp Leu Phe Ala Glu Tyr Arg Ser His
            100                 105                 110

Phe Thr Gly Gly Leu Ala Arg Leu Ala Gln Gly Val Val Phe Pro Ser
        115                 120                 125

Gly Tyr Gln Ala His Gly Ala Thr Glu Thr Cys Pro Gly His Ser Thr
    130                 135                 140

Ile Leu Thr Gly Asn His Pro Ala His Thr Gly Ile Ile Ala Asn Asn
145                 150                 155                 160

Phe Phe Asp Leu Ser Ala Ala Arg Ala Asp Lys Arg Leu Tyr Cys Ala
                165                 170                 175

Glu Asp Glu Thr Val Pro Asp Thr Ser Ser Lys Ser Gly Lys Tyr Ala
            180                 185                 190

Ala Ser Val Asn His Leu Met Val Ala Thr Leu Gly Asp Trp Met Lys
        195                 200                 205

Ala Ala Asn Pro Lys Ala Gln Val Val Ser Val Ala Gly Lys Asp Arg
    210                 215                 220
```

-continued

Ala Ala Ile Met Met Gly Gly Arg Lys Ala Asp Glu Leu Met Trp Leu
225                 230                 235                 240

Phe Pro Gly Gly Leu Thr Ser Tyr Arg Gly Val Ala Leu Ser Pro Val
            245                 250                 255

Ala Gln Gln Ala Ser Thr Ala Ile Ala Ala Ile Ala Ala Pro Arg
        260                 265                 270

Pro Gly Leu Thr Leu Pro Ala Asp Cys Ala Ser His Asp Ile Ala Ile
        275                 280                 285

Pro Ile Gly Asp Lys Gly Ala Thr Val Gly Thr Trp Arg Phe Gln Arg
290                 295                 300

Asp Gly Gly Asp Phe Arg Arg Phe Met Ala Ser Pro Glu Ala Asp Gly
305                 310                 315                 320

Ala Val Leu Ala Ala Gly Ala Ala Leu Arg Ala Ala Arg Lys Met Gly
                325                 330                 335

Glu Gly Asp Thr Thr Asp Leu Leu Ile Leu Gly Leu Ser Ala Thr Asp
            340                 345                 350

Tyr Ile Gly His Gly Thr Gly Thr Glu Gly Ser Glu Met Cys Ile Gln
            355                 360                 365

Met Leu Ala Leu Asp Arg Gln Leu Gly Asp Phe Phe Ala Arg Leu Asp
370                 375                 380

Ala Thr Gly Ile Asp Tyr Met Val Met Leu Thr Ala Asp His Gly Gly
385                 390                 395                 400

His Asp Leu Pro Glu Arg Asn Arg Gln Asn Ala Trp Pro Ala Ala Glu
                405                 410                 415

Arg Val Glu Lys Ser Leu Asp Pro Asp Ala Met Gly Gln Ala Val Ala
            420                 425                 430

Glu Lys Leu Gly Leu Pro Gln Pro Leu Leu Tyr Ser Asp Gly Pro Phe
        435                 440                 445

Gly Asp Met Tyr Leu Ser Lys Ala Leu Thr Pro Ala Gln Arg Lys Ala
        450                 455                 460

Ala Met Ala Glu Leu Val Ala Arg Phe Lys Ala His Arg Gln Val Glu
465                 470                 475                 480

Thr Val Val Thr Gly Glu Glu Leu Ala Ala Arg Pro Ile Ser Lys Gln
                485                 490                 495

Ser Pro Asp Thr Trp Ser Leu Leu Asp Lys Leu Arg Ala Ser Tyr Asn
            500                 505                 510

Pro Gln Arg Ser Gly Asp Phe Ile Val Val Leu Lys Pro Arg Val Thr
        515                 520                 525

Pro Ile Ala Glu Ser Gly Met Gly Tyr Val Ala Thr His Gly Ser Val
        530                 535                 540

Trp Asp Tyr Asp Arg Arg Val Pro Met Leu Phe Trp Arg Lys Gly Leu
545                 550                 555                 560

Thr Gly Phe Glu Gln Pro Asn Ala Val Met Thr Val Asp Ile Leu Pro
                565                 570                 575

Thr Leu Ala Ala Val Ile Gly Val Pro Leu Asp Ala Asp Lys Ile Asp
            580                 585                 590

Gly Arg Cys Leu Asp Leu Leu Ser Gly Pro Glu Ser Ser Cys Arg
        595                 600                 605

<210> SEQ ID NO 2
<211> LENGTH: 1824
<212> TYPE: DNA
<213> ORGANISM: Artificial Sequence
<220> FEATURE:
<223> OTHER INFORMATION: Synthetic Construct

```
<400> SEQUENCE: 2
atgtcacaat cctatgcctg tgcaaatcca ctgtccgccc gccgccgttc gtctcgtcaa      60
ggcttgccat ataggcggct ttcgccgaga ggacagcccg cgccgacgcc ccttgcccgg     120
agaagttgcc ctgtgacgtt caaatatctc gccaccgccc ttgccgccac cctctcgatc     180
gccgccaccg gcgccgtcgt tgcgcaggat agggcggcgc ctgcacctgt tgccccgca      240
gccaaggtca ccgcggccac cccggcgccg aaactggtca tcgccatttc ggtcgatcaa     300
ttctcggccg atctcttcgc cgaatatcgc agccatttca ccggcggcct cgcgcggctc     360
gcccagggcg tcgtcttccc ttcgggctat caggcgcatg gcgcgaccga gacctgcccc     420
ggccattcga cgatcctgac cggcaaccac cccgcgcaca ccggcatcat cgcgaacaat     480
ttcttcgacc tgtcggccgc gcgcgccgac aagcgcctct attgcgccga ggatgagacg     540
gtccccgaca ccagttcgaa gagcggcaaa tatgcggcgt cggtcaatca cctgatggtc     600
gcgacgctcg gcgactggat gaaggccgcc aatccgaagg cgcaggtcgt ctcggtcgcg     660
ggcaaggacc gcgccgcgat catgatgggc ggtcgcaagg ccgacgaact gatgtggctc     720
tttcccggcg ggctgaccag ctatcgcggt gtagcgctgt cgccggtcgc gcagcaggcg     780
agcaccgcca tcgccgccgc catcgccgcg ccgcgtccgg ggctgacgct tcccgccgat     840
tgcgcgtcgc acgacatcgc catccccatc ggcgataaag gcgccaccgt cggcacctgg     900
cgctttcagc gcgacggcgg cgatttccgc gcttcatgg catcgcccga agccgacggc      960
gccgtcctcg ccgcgggcgc gcgctccgc gccgcgcgca agatgggcga gggcgatacc     1020
accgaccttt tgatcctcgg cctgtcggcg accgactata tcggccatgg caccggcacc     1080
gagggcagcg agatgtgcat tcagatgctc gcgctcgacc gccagctcgg cgatttcttc     1140
gcgcggctcg acgcgacggg gatcgattat atggtgatgc tgaccgccga tcacggcggc     1200
cacgacctgc ccgagcgcaa tcgccagaac gcctggccgg ccgccgagcg cgtcgagaaa     1260
tcgctcgatc cggatgcgat gggccaggcg gtcgccgaaa agctcggcct gccgcagccc     1320
ttgctctaca gcgacggtcc tttcggcgac atgtatctgt cgaaggcgct gactccggcg     1380
cagcgcaagg cggcgatggc cgagctggtc gcgcgcttca aggcgcatcg tcaggtcgag     1440
acggtggtga ccggcgagga actggccgcg cggccgatct cgaaacagtc gcccgacacc     1500
tggagcctgc tcgacaagct ccgcgcctcc tataatccgc agcggtcggg cgatttcatc     1560
gtcgtcctga aaccgcgcgt gacgccgatc gccgaatcgg gcatgggcta tgtcgcgacg     1620
cacgggtcgt tgtgggatta tgaccggcgg gtgccgatgc tgttctggcg caagggactc     1680
accgggttcg agcaaccgaa tgccgtgatg acggtggaca ttctcccgac cctcgcggcg     1740
gtgatcgggg tgccgctcga cgcggacaag atcgacggcc gctgcctcga cctcctctcg     1800
gggcccgaga gcagttgccg ctag                                           1824

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
ccggaattcg agctgatcga aagtcgg                                          27

<210> SEQ ID NO 4
<211> LENGTH: 27
<212> TYPE: DNA
```

```
<213> ORGANISM: Artificial Sequence
<220> FEATURE:
<223> OTHER INFORMATION: Synthetic Construct

<400> SEQUENCE: 4
ccggaattcc tagccttcga tgccgat                                           27

<210> SEQ ID NO 5
<211> LENGTH: 2157
<212> TYPE: DNA
<213> ORGANISM: Artificial Sequence
<220> FEATURE:
<223> OTHER INFORMATION: Synthetic Construct

<400> SEQUENCE: 5
ccggaattcg agctgatcga aagtcggtgt gggggtattg gtcacggcca tctccaggtt        60
ggcggattgc gcaggacaaa gtgcaacagc tgtgccaagg tctgaaaacc gacttcaagg       120
tattgttttt caatgtgttt ctaattttta gaatgatcgg agcgagcgaa attaagccgc       180
gcttgcgcag gcttttaag catttgatca attgcccaag gccgcttgag caaatgctca       240
tggcgcagct gaaggctgat ctctagcact aaagtcactg ccgtcgattg atcatttggt       300
tgacttttgc cagatactga ggtcggctat ggggagctgg cgcaggtgaa aaaactgccg       360
attttcccca tgaccccatc tggaatcgcc gcctgcttg cgctatagcg gcgaccctga       420
tttccccatc taaaaataaa taggggcctc gcttacatgc cgatcaagta caagcctgaa       480
atccagcact ccgatttcaa ggacctgacc aacctgatcc acttccagag cacggaaggc       540
aagatctggc ttggcgaaca acgcatgctg ttgctgcagg tttcagcaat ggccagcttt       600
cgccgggaaa tggtcaatac cctgggcatc gaacgcgcca agggcttctt cctgcgccag       660
ggttaccagt ccggcctgaa ggatgccgaa ctggccagga gcttagacc gaatgccagc       720 gagtacgaca tgttcctcgc cggcccgcag ctgcattcgc tcaagggtct ggtcaaggtc       780
cgccccaccg aggtcgatat cgacaaggaa tgcgggcgct tctatgccga gatggagtgg       840
atcgactcct tcgaggtgga aatctgccag accgacctgg ggcagatgca agacccggtg       900
tgctggactc tgctcggcta cgcctgcgcc tattcctcgg cgttcatggg ccgggaaatc       960
atcttcaagg aagtcagctg ccgcggctgc ggcggcgaca agtgccgggt cattggcaag      1020
ccggccgaag agtgggacga cgttgccagc ttcaaacagt atttcaagaa cgaccccatc      1080
atcgaggaac tctacgagtt gcaatcgcaa ctggtgtcgc tgcgtaccaa cctcgacaaa      1140
caggaaggcc agtactacgg catcggtcag accccggcct accagaccgt gcgcaatatg      1200
atggacaagg ccgcacaggg caaagtctcg gtgctgctgc ttggcgagac cggggtcggc      1260
aaggaggtca tcgcgcgtag cgtgcacctg cgcagcaaac gcgccgccga gccctttgtc      1320
gcggtgaact gtgcggcgat cccgccggac ctgatcgagt ccgaattgtt cggcgtggaa      1380
aaaggcgcct tcaccggcgc cacccagtca cgcatgggcc gcttcgagcg ggccgacaag      1440
ggcaccatct tccttgacga ggtgatcgaa ctcagcccgc gcgctcaggc cagtttgctg      1500
cgcgtgctgc aagaaggcga gctggagcga gttggcgaca accgcacgcg caagatcgac      1560
gtaagggtta tcgcagccac ccacgaggac ctggccgaag cggtcaaggc cgggcgtttt      1620
cgcgccgacc tgtactaccg gctgaacgtt ttccgggtgg cgatcccggc gttgcgcgaa      1680
cgccgcgagg acattccact gctggttgag cacttccttc agcgcttcca ccaggagtac      1740
ggcaagagaa ccctcggcct ttcagacaaa gccctggagg cctgcctgca ttacagttgg      1800
ccgggcaata tccgtgagct ggagaacgtc atcgagcgcg gcatcatcct caccgatccg      1860
```

```
-continued aacgaaagca tcagcgtgca ggcgctgttc ccacgggcgc cggaagagcc gcagaccgcc    1920
agcgagcggg tgtcgtcgga cggcgtgctg attcagccag gcaatggcca gggcagttgg    1980
atcagccagt tgttgagcag cggcctgagc ctcgacgaga tcgaggaaag cctgatgcgc    2040
aaagccatgc aacaggccaa ccaaaacgtc tccggtgccg cgcgcttgct cggcctaagc    2100
cgaccggcac tggcctatcg gctgaagaaa atcggcatcg aaggctagga attccgg      2157

<210> SEQ ID NO 6
<211> LENGTH: 70
<212> TYPE: DNA
<213> ORGANISM: Artificial Sequence
<220> FEATURE:
<223> OTHER INFORMATION: Synthetic Construct

<400> SEQUENCE: 6
acctggagat ggccgtgacc aatacccca caccgactt cgatcagctc atgagtaaag      60
gagaagaact                                                           70

<210> SEQ ID NO 7
<211> LENGTH: 70
<212> TYPE: DNA
<213> ORGANISM: Artificial Sequence
<220> FEATURE:
<223> OTHER INFORMATION: Synthetic Construct

<400> SEQUENCE: 7
cggataacaa tttcacacag gaaacagcta tgaccatgat tacgccaagc ttatttgtag    60
agctcatcca                                                           70

<210> SEQ ID NO 8
<211> LENGTH: 34
<212> TYPE: DNA
<213> ORGANISM: Artificial Sequence
<220> FEATURE:
<223> OTHER INFORMATION: Synthetic Construct

<400> SEQUENCE: 8
gggaattcca tatgtcacaa tcctatgcct gtgc                                34

<210> SEQ ID NO 9
<211> LENGTH: 44
<212> TYPE: DNA
<213> ORGANISM: Artificial Sequence
<220> FEATURE:
<223> OTHER INFORMATION: Synthetic Construct

<400> SEQUENCE: 9
ccgctcgagt gaaatccttc cctcgatgcg gcaactgctc tcgg                     44
```